United States Patent
Themelis (10) Patent No.: US 12,150,720 B2
(45) Date of Patent: *Nov. 26, 2024

(54) SURGICAL MICROSCOPE WITH GESTURE CONTROL AND METHOD FOR A GESTURE CONTROL OF A SURGICAL MICROSCOPE

(71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,511

(22) Filed: Jul. 17, 2023

(65) Prior Publication Data

US 2023/0355323 A1    Nov. 9, 2023

Related U.S. Application Data

(63) Continuation of application No. 17/705,457, filed on Mar. 28, 2022, now Pat. No. 11,744,653, which is a
(Continued)

(30) Foreign Application Priority Data

Aug. 16, 2016 (EP) .................................. 16184312

(51) Int. Cl.
*A61B 34/00* (2016.01)
*A61B 90/20* (2016.01)
(Continued)

(52) U.S. Cl.
CPC .......... *A61B 34/25* (2016.02); *G02B 21/0012* (2013.01); *G02B 21/22* (2013.01);
(Continued)

(58) Field of Classification Search
CPC .... A61B 34/25; A61B 90/20; G02B 21/0012; G02B 21/22; G02B 21/364; G02B 21/368; G06F 3/017; G06F 3/04847; G06F 3/0304
See application file for complete search history.

(56) References Cited

U.S. PATENT DOCUMENTS 7,493,153 B2    2/2009   Ahmed et al.
7,768,701 B2    8/2010   Namii et al.
(Continued)

FOREIGN PATENT DOCUMENTS

DE    10335369 A1    3/2005
DE    102012220195 A1    5/2014
(Continued)

*Primary Examiner* — Keith M Raymond
*Assistant Examiner* — Sean A Frith
(74) *Attorney, Agent, or Firm* — Hodgson Russ LLP (57) ABSTRACT

The present invention relates to a surgical microscope with a field of view and comprising an optical imaging system which images an inspection area which is at least partially located in the field of view, and to a method for a gesture control of a surgical microscope having an optical imaging system. The surgical microscope further comprises a gesture detection unit for detection of a movement of a surgical instrument, the gesture detection unit having a detection zone which is located between the inspection area and the optical imaging system and is spaced apart from the inspection area, and the gesture detection unit being configured to output a control signal to the optical imaging system depending on the movement of the surgical instrument in the detection zone, the optical imaging system being configured to alter its state depending on the control signal.

16 Claims, 5 Drawing Sheets

Related U.S. Application Data continuation of application No. 15/650,877, filed on Jul. 15, 2017, now Pat. No. 11,284,948.

(51) Int. Cl.
| | | |
|---|---|---|
| *G02B 21/00* | (2006.01) | |
| *G02B 21/22* | (2006.01) | |
| *G02B 21/36* | (2006.01) | |
| *G06F 3/01* | (2006.01) | |
| *G06F 3/03* | (2006.01) | |
| *G06F 3/04847* | (2022.01) | |

(52) U.S. Cl.
CPC .......... *G02B 21/364* (2013.01); *G06F 3/017* (2013.01); *G06F 3/04847* (2013.01); *A61B 90/20* (2016.02); *G02B 21/368* (2013.01); *G06F 3/0304* (2013.01)

(56) References Cited

U.S. PATENT DOCUMENTS

| 9,330,477 | B2 | 5/2016 | Rappel | |
| 9,465,444 | B1 | 10/2016 | Ramaswamy | |
| 9,645,652 | B2* | 5/2017 | Kelsey | G06F 3/017 |
| 9,785,247 | B1 | 10/2017 | Horowitz et al. | |
| 11,284,948 | B2* | 3/2022 | Themelis | G02B 21/22 |
| 11,744,653 | B2* | 9/2023 | Themelis | A61B 34/25 |
| | | | | 600/429 |
| 2004/0254454 | A1 | 12/2004 | Kockro | |
| 2008/0136775 | A1 | 6/2008 | Conant | |
| 2009/0059363 | A1 | 3/2009 | Straehle et al. | |
| 2010/0245557 | A1 | 9/2010 | Luley, III et al. | |
| 2010/0315335 | A1 | 12/2010 | Villar et al. | |
| 2011/0235168 | A1 | 9/2011 | Sander | |
| 2012/0274550 | A1 | 11/2012 | Campbell et al. | |
| 2012/0323364 | A1 | 12/2012 | Birkenbach et al. | |
| 2012/0327125 | A1 | 12/2012 | Kutliroff et al. | |
| 2014/0022171 | A1 | 1/2014 | Yanai | |
| 2014/0063226 | A1 | 3/2014 | Kawata et al. | |
| 2014/0351753 | A1 | 11/2014 | Shin et al. | |
| 2014/0361985 | A1 | 12/2014 | Arai | |
| 2015/0224643 | A1 | 8/2015 | Emsperger et al. | |
| 2015/0305813 | A1 | 10/2015 | Tashiro | |
| 2015/0324000 | A1 | 11/2015 | Park et al. | |
| 2015/0342697 | A1 | 12/2015 | Saur et al. | |
| 2016/0018897 | A1* | 1/2016 | Nagai | G02B 27/017 |
| | | | | 345/156 |
| 2016/0027199 | A1 | 1/2016 | Cao et al. | |
| 2016/0180046 | A1 | 6/2016 | Sezeur et al. | |
| 2016/0266764 | A1 | 9/2016 | Aurongzeb et al. | |
| 2016/0331584 | A1 | 11/2016 | Ren et al. | |
| 2016/0364007 | A1 | 12/2016 | Kamovich et al. | |

FOREIGN PATENT DOCUMENTS

| DE | 102014106865 A1 | 11/2015 |
| DE | 102014007909 A1 | 12/2015 |
| EP | 2547278 A1 | 1/2013 |
| JP | 2015521913 A | 8/2015 |
| WO | 2015172021 A1 | 11/2015 |

* cited by examiner

SURGICAL MICROSCOPE WITH GESTURE CONTROL AND METHOD FOR A GESTURE CONTROL OF A SURGICAL MICROSCOPE

CROSS REFERENCE TO RELATED APPLICATIONS

This application is a continuation of U.S. application Ser. No. 17/705,457 filed Mar. 28, 2022, which is a continuation of U.S. application Ser. No. 15/650,877 filed Jul. 15, 2017, which claims priority to European Application No. 16184312.3 filed Aug. 16, 2016, the entire disclosures of which are incorporated by reference herein.

FIELD OF THE INVENTION

The invention relates to a surgical microscope with a field of view and comprising an optical imaging system which images an inspection area which is at least partially located in the field of view. The invention further relates to a method for a gesture control of a surgical microscope having an optical imaging system.

BACKGROUND OF THE INVENTION

Surgical microscopes are optical devices intended to provide low magnification at the operation area and a relatively large working distance so that the operation area is easily accessible for the surgeon to perform surgical operations. The operation area or inspection area is commonly imaged by an optical imaging system which provides an image of the inspection area either to the eyes of the surgeon via a commonly stereoscopic eyepiece and/or via a monitor or screen which displays the image imaged by the optical imaging system and detected by a camera recording said image.

Surgical microscopes are designed to minimize the disturbance to the surgeon to maintain his or her focus on the operation. However, the surgical workflow is disturbed when the surgeon changes microscope parameters such as exemplarily focus, zoom and field of view, i.e. the operation or inspection area currently viewed. Altering such microscope parameters requires the surgeon to free his or her hand from surgical tools to operate the microscope's interaction means as, for instance, microscope handles, buttons and adjustment wheels.

Consequently, in order to change any microscope parameters during an operation, the surgeon applying a state of the art surgical microscope is required to put down the surgical tools on a workstation or the like for reaching to and operating the microscope's interaction means. With such adjustment operations of the surgeon, the surgical workflow is interrupted and can lead to a loss of focus for the surgeon, which inconveniences the surgeon as he or she must look up from the microscope eyepiece and adapt to different ambient light conditions. Furthermore, such adjustments may delay the operation on a patient. Additionally, due to the need to put down the surgical tools, the risk of contamination increases. Besides, the surgeon might use sub-optimal microscope settings, i.e. settings that still have room for improvement, in order to avoid the above-mentioned inconveniences and delays.

The above inconveniences led to the development of prior art solutions such as foot switches and a mouth switches which allow the surgeon to control the microscope with either his or her foot or mouth. Although the use of foot switches or mouth switches may overcome some of the above disadvantages, such prior art solutions remain non-intuitive, require training and are not convenient for all surgeons. Furthermore, a foot switch is not suitable to control the field of view of the surgical microscope and is not as accurate as a hand control. Therefore, the microscope handles remain as the main method to control and interact with the microscope.

SUMMARY OF THE INVENTION

It is therefore one object of the present invention to provide a surgical microscope which further improves the existing surgical microscopes, especially in view of an undisturbed operation workflow, respectively an operation workflow with disturbances by, for instance, adjustments kept to a minimum.

Furthermore, it is one object of the present invention to provide a method providing the same advantages as the surgical microscope.

For the surgical microscope mentioned in the beginning, this goal is achieved according to the invention in that the surgical microscope further comprises a gesture detection unit for detection of a movement of an object such as at least one of a finger and a tool, and in that the gesture detection unit is connected to the optical imaging system via a signal line and in that the gesture detection unit is configured to output a control signal via the signal line to the optical imaging system depending on the movement of the object, the optical imaging system being configured to alter its state depending on the control signal.

For the method mentioned in the beginning, this goal is achieved according to the invention in that the method comprises the steps of contactlessly detecting a movement of an object such as at least one of a finger and a tool with respect to a reference point, in particular to a gesture detection unit and/or contactlessly detecting the distance of the object to the reference point and controlling the optical imaging system depending on the movement of the object.

In the following, further embodiments of the invention are described. Each of the further embodiments described herein below has its own advantage and technical effect and can thus be arbitrarily combined with any other embodiment described.

The movement of the object may be detected next to the surgical microscope, preferentially within the reaching area of the surgeon. More preferentially, the movement of the object is detected between the optical imaging system and the inspection area.

A contactless detection of a movement or a distance may be realized by optical or ultrasonic means.

Detection of the movement of the object next to the surgical microscope has the advantage that the surgeon may locate his/her hands on the side of the microscope acting as virtual handles which may allow him/her to turn or relocate the microscope without touching anything.

The reference point of the gesture control may be predetermined and therefore preferentially be the gesture detection unit. The reference point may as well be located in the inspection area. In any case, the absolute position of the object may only be used for calculation of a relative movement or a relative position of the object.

Such an inventive surgical microscope has the advantages that the surgeon maintains his or her focus on the surgical procedure, that no delays are generated during an adjustment or readjustment of the surgical microscope as controlling the surgical microscope by gestures is quicker than by the microscope handles and that any risks of contamination are minimized as the surgeon does not need to put down the surgical tools for adjustment or readjustment of the surgical microscope. Additionally, controlling the surgical microscope by hand is more accurate than, for instance, using a foot switch or using a mouth switch. Thus, one advantage of the invention is to provide a surgical microscope which supports the surgeon and the surgical workflow without distracting the surgeon or disturbing the surgical workflow.

Further advantages of the inventive surgical microscope with gesture control is an intuitive operation of the surgical microscope, the possibility of an interactive operation of the surgical microscope which is similar to operating systems of mobile phones and the possibility to implement the inventive gesture control with components already present in the surgical microscope, i.e. a 3-D camera or a differential interference contrast unit (DIC-unit), which renders the upgrade of existing surgical microscopes as inexpensive. Furthermore, the present invention does not alter the appearance of existing surgical microscopes as it does not add any visible components such as buttons, foot switches or mouth switches to the surgical microscope.

A gesture is to be understood as a movement of an object such as a finger or a tool, as a relative movement of two objects to each other, or as a rotation of one or more objects. The rotation of one or more objects may be performed around any of the spatial axes, e.g. perpendicular or parallel to the imaging axis. Rotations around the spatial axes may be arbitrarily combined.

The inventive surgical microscope may comprise a set of complicated gestures detectable by the detection unit, for instance gestures like thumbs up, open palm or closed palm. Furthermore, detection of an arbitrary number of fingers, for instance two fingers may also be interpreted as a gesture by the gesture detection unit.

A movement of an object may occur in a plane essentially parallel to the operation area, which may be referred to as horizontal movement. Movements of the object parallel to the imaging axis may be referred to as vertical movements.

The operation area, which may also be called an inspection area, is to be understood as a portion of a patient to be operated on or to be inspected, which portion may also be addressed as the field of view of the surgical microscope. The field of view of the surgical microscope is defined by the numerical aperture of a microscope's objective and the distance between the objective and the inspection area. The inspection area is essentially perpendicular to an optical axis of the optical imaging system, in particular, essentially perpendicular to the optical axis of the optical components of the optical imaging system facing towards the inspection area, i.e. the optical axis of the microscope objective currently applied.

The surgical microscope may comprise an arm holding the microscope, which arm may be attached to a stand. The surgical microscope is commonly not equipped with a stage but may be adapted to be modified with an optional stage.

The movement of the object may be detected inside the field of view of the optical imaging system. In other words, a movement of the object may be detected in the field of view of the optical imaging system, i.e. the object and its movement is imaged by the optical imaging system and can be seen by the surgeon.

The surgical microscope may further comprise an eyepiece control unit, which detects whether one, both or neither eyepieces of the generally stereoscopic eyepiece are used. This detection may be understood as an approaching sensor which may activate the eyepiece if the surgeon approaches his/her face to the eyepiece.

If the surgeon only approaches one eye to the stereoscopic eyepiece, only the eyepiece used may be activated, i.e. provided with the imaged operation area. In order to avoid disturbances to the surgeon, the non-used eyepiece may be deactivated, i.e. no disturbing light on the imaged inspection or operation area is transmitted through the non-used eyepiece.

If neither of the two eyepieces of the stereoscopic eyepiece is used, the surgical microscope may initiate turning off the illumination. Turning off the illumination may preferentially only performed after a predetermined delay time. Brief interruptions to the surgeon may therefore not be sufficiently long to initiate turning of the illumination of the surgical microscope.

The detection of only one eyepiece used may also be interpreted as a gesture of the surgeon. If the surgical microscope detects that only one eyepiece is used, the gesture detection unit may interpret this gesture as a selection, e.g. right-left selection which may exemplarily be a selection of illumination or magnification during the initialization of the surgical microscope.

In another embodiment of the inventive surgical microscope, such a movement of the object may be performed and detected adjacent to the field of view of the optical imaging system, in a direction perpendicular to the optical axis of the objective facing towards the inspection area. Preferentially, detection is performed on a side of the field of view which may be conveniently reached by the surgeon with his or her finger and/or tool, whereas in this embodiment of the inventive surgical microscope, the finger and/or tool is not visible to the surgeon via the eyepiece or the miscroscope's screen.

The gesture detection unit detects the movement of the object by optical detection, i.e. is contactless. The control signal may be output via an electric line in form of an analogue or digital signal but may as well be wirelessly transmitted to a receiver. The wireless transmission of the control signal is, for instance, advantageous if the control signal is to be transmitted from the gesture control unit towards a member of the surgical microscope to be controlled, which member is located distant to the gesture detection unit, such that an electric line would increase the risk of accidents, e.g. the risk of stumbling over the electric line.

The gesture detection unit may be integrally provided with the surgical microscope, i.e. it may be integrated into any existing surgical microscope.

It is also conceivable that the gesture detection unit is embodied as a separate unit which is attached to the surgical microscope and connected to the surgical microscope wire lines or wireless connection means.

In a first advantageous embodiment of the inventive surgical microscope, the gesture detection unit comprises a detection zone which is located between the inspection area and the optical imaging system and which detection zone is spaced apart from the inspection area, wherein gesture detection of the gesture detection unit is limited to movements of the object in the detection zone.

Such a detection zone is to be understood as a three-dimensional volume in which gestures, i.e. movements of the object are detected. Outside this detection zone, movements of the object do not result in a control signal output to the optical imaging system. Locating the detection zone spaced apart from the inspection area has the advantage that during operation on a patient performed in the inspection area, the surgical microscope will not be adjusted or readjusted by the surgeon, in particular not by a tool, e.g. a scalpel or the like. That is to say the portion of the inspection area that is imaged by the optical imaging system is not altered and the surgeon is not distracted by, for instance, a change in the field of view. However, by moving a finger into the detection zone, the surgeon may adjust or readjust the surgical microscope.

In a second advantageous embodiment of the inventive surgical microscope, the detection zone overlaps the inspection area at least in sections. In this embodiment, the portion of the inspection area which is imaged by the optical imaging system and which can be seen by the surgeon via an eyepiece or a screen, also images the moved object which has the advantage that the movement of the object may be accurately monitored by a surgeon.

The detection zone may extend beyond the field of view of the optical imaging system. Thus, the detection of the movement of the object is performed outside the field of view in a detection zone not being limited by the field of view. The detection zone extending beyond the field of view may be advantageous for certain adjustments of the surgical microscope such as, for instance, a pan (shifting the area to be operated on or to be inspected in a plane being essentially perpendicular to the optical axis of the microscope's objective) or a zoom (the change of magnification).

In another advantageous embodiment of the inventive surgical microscope, the gesture detection unit further comprises a movement detection module for differentiating three-dimensional movements of the object in the detection zone, which movement detection module is connected to the gesture detection unit via a movement-data line and which movement detection module is adapted to output a movement-data signal via the movement-data line to the gesture detection unit depending on the movement of the object.

The movement detection module has the advantage that it allows to differentiate movements occurring in a detection plane which is essentially perpendicular to the optical axis of the microscope's objective currently applied, i.e. the detection plane is essentially parallel to the inspection area and is located within the detection zone. As the detection zone extends along the optical axis of the microscope's objective currently applied, a manifold of different detection planes is conceivable.

The movement detection module may differentiate between movement of the object in the detection plane and along a direction essentially perpendicular to the detection plane.

The movement detection module may further comprise a distance detection unit which may be adapted to provide a distance signal which depends on the distance of the object to the distance detection unit. The distance detection unit may provide the distance signal via a distance line to a binary comparator which detects whether the object is within the detection zone in a direction along the optical axis of the microscope's objective currently applied.

The movement detection module may further be adapted to detect movements representing a combination of movements in the detection plane and perpendicular to the detection plane, that is to say, three-dimensional movements.

In another advantageous embodiment of the inventive surgical microscope, the gesture detection unit further comprises a relationship mapping unit which is connected to the movement detection module via the movement-data line and which relationship mapping unit is adapted to map relationships between a movement of the object and a control signal, which control signal is provided via the signal line to the optical imaging system.

The relationship mapping unit may be adapted to provide a relationship map which may be stored in a non-transient storage medium, the relationship map being a bi-unique assignment of a specific control signal to a movement pattern of the object.

The relationship mapping unit may further comprise a resemblance unit which receives the movement-data of the object and outputs a signal in which the specific movement pattern, which is found to correspond to the measured movement pattern, is coded.

The relationship mapping unit may be connected to a computing unit or may comprise the computing unit. The computing unit may be a microcontroller, a personal computer or the like. The computing unit may allow an interaction with a user in general or only during service and maintenance. The computing unit may further be adapted to record any user specific movements of the object in the relationship map.

In another advantageous embodiment of the inventive surgical microscope, the optical imaging system comprises movable mechanical components, the position of which depends on the control signal. This embodiment has the advantage that the surgeon may control the surgical microscope mechanically, e.g. moving the field of view relative to the portion of the inspection area in order to image different portions of, for instance, the patient and the operation area.

Furthermore, it is conceivable that mechanical components of the surgical microscope comprise movable illumination means, which may be adjusted in terms of their position and/or light intensity and/or filters applied and/or similar possible adjustments to illumination means.

In another advantageous embodiment of the inventive surgical microscope, the optical imaging system comprises a projection unit, which projection unit is optically connected to the optical imaging system and which projection unit is adapted to project optional and/or interactive images on at least one interaction portion, the at least one interaction portion at least partially overlaps with the imaged inspection area.

The projection unit has the advantage of increased versatility and interaction of the surgical microscope.

The projection unit may be optically connected to the optical imaging systems by means of beam combiners, which allow overlaying images. In a further embodiment, the projection unit may project the optional and/or interactive images directly as a real image onto the inspection area, whereas for the reasons of visibility, an overlay of virtual images is preferred.

The interaction portion is to be understood as a portion of the imaged inspection area, which interaction portion is preferably located at the edges, even more preferably located in the corners of the imaged inspection area. The interaction portion is thus a virtual section of the imaged inspection area, which virtual section may only be seen via the eyepiece or the screen of the surgical microscope.

The overlay of the optional and/or interactive images by the projecting unit may be performed, for instance, by an opaque or a semi-transparent overlay.

The projection unit may project images containing parameters of the surgical microscope or, for instance, vital signs of the patient. The projected images may furthermore act as projected virtual buttons whose functionality will be explained with reference to the method in the following.

The inventive method introduced above comprises mainly two steps. In the first step, a movement of the object is optically detected, by i.e. in a contactless manner. The detection of the movement refers to a movement in a plane essentially perpendicular to the optical axis of the microscope objective currently applied, and to the detection of the distance of the object from the gesture detection unit. Thus, the method is adapted to detect a three-dimensional movement of the object.

In the second step, the gesture detection unit provides a control signal to the optical imaging system for controlling said optical imaging system depending on the movement of the object.

In a first advantageous embodiment of the inventive method, the method further comprises the step of providing distance and movement data of the object to a computing unit. The distance and movement data of the object may be provided via a data line, wherein the data may be encoded analogue or digital. The computing unit may be adapted to temporarily store the received distance and movement data of the object.

In a second advantageous embodiment of the inventive method, the method further comprises the step of differentiating the detected movement of the object. The first step of differentiating may be the distinction between a movement of the object in a plane oriented parallel to the inspection area, a movement in a direction essentially perpendicular to the inspection area, i.e. parallel to the optical axis of the microscope objective currently applied, or a combined movement of the former two.

In another advantageous embodiment of the inventive method, a further step of comparing the movement of the object with predetermined movement patterns is comprised. During this step, the distance and movement data of the object, which data may be stored by the computing unit, is compared with predetermined movement patterns which may, for instance, be stored in a relationship map, which relationship map is read and compared with the measured distance and movement data of the moving object. For each of the entries in the relationship map, a resemblance value indicating the resemblance of the according predetermined movement patterns with the measured movement of the object may be output, the resemblance values may be compared and put in order, whereas the highest of the resemblance values, which indicates the highest resemblance between the measured movement and the predetermined movement pattern, may be output.

In another embodiment of the inventive method, it is advantageous if the method further comprises the step of controlling movable mechanical components of the surgical microscope depending on the movement of the object.

In this step of the method, the control signal is provided by the gesture detection unit via a signal line or via a wireless connection to a receiver of the surgical microscope, which receiver receives and interprets the control signal and subsequently initiates the alternation of the state of the surgical microscope depending on the control signal received.

In yet another advantageous embodiment of the inventive method, the method further comprises the steps of projecting at least one optional and/or interactive image onto at least one interaction portion of the imaged inspection area, comparing the movement of the object with predetermined interaction movement patterns, and controlling the optical imaging system and/or the surgical microscope depending on the movement of the object within the at least one interaction portion.

Such an embodiment has the advantage that it comprises an increased versatility and functionality, which functionality is executable upon a contactless optical input by the surgeon.

In this embodiment, the optional and/or interactive image projected onto at least one interaction portion of the imaged inspection area may comprise the image of the data of the surgical environment and/or the patient. Such a projected image may represent vital signs of the patient or parameters of the surgical microscope or similar data relevant to the surgeon.

The method may be adapted to compare the position of the object with the position of the at least one interaction portion of the imaged inspection area and may further initiate loading of a second relationship map if the object is detected to be located within the interaction portion. The second relationship map may comprise a different set of predetermined movement patterns as compared to the first relationship map which is loaded if the object is detected in the detection zone outside the interaction portion.

After detecting an off-line movement, this embodiment of the method may initiate a change of surgical microscope settings, such as the lighting or imaging mode of the surgical microscope, saving an image of the currently viewed portion of the inspection area or similar functionality to be performed.

An off-line movement is to be understood as a movement which initiates an operation which is performed after the user interacts with the object, i.e. after the movement of the object is performed. Exemplarily, the change of the microscope's imaging mode may be performed after the vertical movement of the object, this movement being similar to a mouse click, is detected. On the contrary, online movements directly initiate an operation during the movement of the object as for instance pan, zoom or tilt of the imaged inspection area.

In a further advantageous embodiment of the inventive method, the method further comprises the steps of optically detecting the object, comparing the detected object with predetermined object patterns for determination of the type of the object, and selecting one of at least two relationship maps according to the type of the object. This embodiment of the method has the advantage that the possible parameters which are controllable by the object depend on the object. That is to say, if a scalpel is detected, the possible operations depending on the movement of the scalpel may be different to the possible operations if a finger is detected. This may, for instance, be advantageous in the sense that the movement of the patient may be deactivated if a scalpel is detected in order to avoid unintentional cuts by the scalpel.

Furthermore, the relationship map loaded upon detection of a scalpel may comprise more precise adjustment steps then the relationship map, which is loaded if a finger is detected. By such a distinction, the coarse alignment of the surgical microscope may be performed with the finger of the surgeon, whereas a fine adjustment may be performed if the scalpel is used.

In this embodiment of the method, a further step of deciding which object, e.g. a scalpel or a finger initiates loading of the according relationship map if two or more different objects are detected, may be comprised. A certain subset of operations of the surgical microscope mapped to a movement of the object may be present in all operation modes, whereas in the different operation modes, the adjustment may occur in a coarse or fine manner.

Gesture detection of the inventive surgical microscope and method may be based on suitable models and algorithms, for instance, 3D model-based algorithms, appearance-based algorithms, skeletal-based algorithms, and similar approaches.

The detection of a gesture may be performed by, exemplarily, stereo cameras, depth-aware cameras, single cameras or a multitude of distance detection units.

The inventive method in any of the above described embodiments is performed by a non-transitory storage medium of an appropriate type. The non-transitory storage medium may, for instance, be an optical storage medium like a compact disc or a digital versatile disc, a magnetic storage medium as a floppy disk or hard disk drive or a non-transitory storage medium based on the storage of electrical charge (flash memory). The non-transitory storage medium may be located in a microcontroller or personal computer which personal computer may further provide input and output means to the user.

In the following, some exemplary possible movements of the object will be presented with an according possible adjustment operation of the surgical microscope.

For the following explanation, an exemplary coordinate system is introduced comprising 3 axes being oriented perpendicular to each other, an x-axis and a y-axis being located in a plane parallel to the inspection area and a z-axis being oriented essentially perpendicular to the inspection area. With respect to the imaged portion of the inspection area which can be seen by the surgeon, the x-axis may be oriented such that it extends from the left side of the image seen by the surgeon to the right side of the image seen by the surgeon. The y-axis may be oriented perpendicular to the x-axis and may extend from the lower side of the image seen by the surgeon to the upper side of the image seen by the surgeon. The z-axis may be oriented out of the inspection area towards the optical imaging system of the surgical microscope.

In such a defined coordinate system, a movement of one single object may be performed along the x-axis, along the y-axis and along a direction composed of a movement along the x-axis and a movement along the y-axis. Such a movement detected by the gesture detection unit may initiate a movement (scrolling/pan) of the imaged portion of the inspection area with a fixed point of the image located at the position of the object moving along with the object.

A further possible movement of the object is along a trajectory describing a semi-circle or an angular section of a circle. Such a movement of the object, the fixed point of the image may initiate the imaged portion of the inspection area to rotate around the image center.

A movement of the object along the z-axis may result in a change of the microscope focus, i.e. altering the working distance. In order to avoid altering the working distance during a movement of the object intended to move the field of view, initiation of the change of a working distance may be limited to a portion of the imaged inspection area, which portion may be located distal to the center of the imaged inspection area.

It may also be possible to control the illumination, for instance, in terms of the intensity and illumination mode depending on the movement of the object. It is conceivable that a stripe-shaped section of the imaged inspection area located at the upper edge of the image seen by the surgeon may be applied for changing of the illumination intensity. Thus, it may be possible to move the object from left to right in the section located at the upper edge of the image in order to increase illumination intensity, respectively from right to left to decrease illumination intensity.

Other microscope parameters that may be controllable by movement of the object are the polarization of the illumination light source, the mode of illumination (for instance white light, narrowband imaging, green light) and possible filters introduced in the light path of the optical imaging system.

Furthermore, a movement of the object along the z-axis may be interpreted as a user input similar to a mouse click. Especially in combination with a projection unit which projects additional and/or interactive images onto the imaged inspection area, the surgeon may trigger predetermined functions of the surgical microscope or its computing unit by locating the object (the surgeon's finger or the scalpel) below the at least one projected image and performing a movement of the object along the z-axis. With such a movement along the z-axis in the interaction portion of the imaged inspection area, the function related to the according interaction portion may be launched. Such a function may, for instance, switch the surgical microscope to a different imaging mode.

It is also possible that the images projected onto the interacting portions of the imaged inspection area refer to different modes of the focus and a movement of the object along the Z-direction in such an interaction portion may switch the focus from manual to local or the outer focus on and/or of.

Further, it is possible that the gesture detection unit detects two or more objects at the same time, wherein the two different objects may be moved towards each other or away from each other. Such a detected combination of movements may generate a control signal initiating the optical imaging system to zoom out or zoom in, i.e. to alter the magnification of the surgical microscope.

Further possible combinations of a combined movement of the two objects may result in a tilt of the inspection area, which may be useful if the optical axis of the objective currently applied is not oriented perpendicular to the inspection area. Furthermore, different combinations of rotational movement and tilt of the inspection area are conceivable and programmable by an according relationship map, i.e. by storing such predetermined movement patterns in said relationship map.

In particular, the above-described gestures for the zooming in, zooming out or moving the field of view are very similar to those gestures commonly used in smartphones and therefore are rather familiar to the surgeon and no intensive training, for instance, in the case of foot switches and mouth switches is necessary.

The inventive surgical microscope and the inventive method for gesture control of the surgical microscope may further comprise and on/off gesture which initiates an activation or deactivation of the gesture control. Any possible gesture may activate or deactivate the gesture control, for instance a double virtual click with an object or a finger, locating the object or the finger on a certain area of the screen or in a certain area of the detection zone, wherein the object or the finger may perform a click in this area or may remain there for a few seconds for activation or deactivation of the gesture control.

Furthermore, activation or deactivation of the gesture control may be performed by the same gesture or by different gestures, whereas activation or deactivation may also be perfomed by audio comments, physical buttons of the surgical microscope, by the use of the eyepiece or by complicated gestures with the surgeon's hands, fingers or object. Those complicated gestures may preferentially be performed next to the microscope, i.e. not in between the object and the imaged area. Especially complicated gestures have the advantage that the gesture control may not unintentionally be activated or deactivated by the surgeon.

The surgical microscope may comprise an assistant's eyepiece which may be located to the side of the surgeon's eyepiece and which assistant's eyepiece may image the inspection area, such that an assistant may follow the operation by observing the surgeon's measures in the inspection area without disturbing the surgeon. Also the assistant's eyepiece may comprise a sensor system detecting whether the assistant eyepiece is used. If the surgical microscope detects that the surgeon's eyepiece is not used, whereas solely the assistant's eyepiece is used, the field of view imaged through the assistant's eyepiece may adapt to the position of the observer using the assistant's eyepiece, e.g. rotate by 90°, whereas also the environment of the gesture control may rotate by 90°.

Therefore the assistant's eyepiece may also be used as a surgeon's eyepiece if the position of the assistant's eyepiece is more convenient to the surgeon.

The surgical microscope may further comprise a feedback generator which may be adapted to output a feedback signal transmitted to visualization means, as for instance a projection unit or illumination means. A feedback signal may also be transferred to audio means, i.e. a speaker which generates a sound corresponding to a certain gesture and giving an audible feedback to the surgeon. Furthermore, the feedback signal may be transmitted to mechanical feedback means as for instance a vibration element indicating the detection of a certain gesture.

The feedback generator may be adapted to solely generate feedback indicating the detection of a gesture, or performing the action relating to the gesture, but may also be adapted to indicate different microscope functions not related to the gesture control as for instance reaching a maximum zoom, indicating an error, saving an image or if the patient's vitals require attention.

In the following, the invention is exemplarily described with reference to the accompanying figures. In the figures, elements providing the same function and/or technical effect are assigned with identical reference numerals.

The combination of features shown in the figures and described below is only an example. Individual features can be added or omitted if the technical effect of that particular feature as described above is needed or may be omitted for a particular application.

BRIEF DESCRIPTION OF THE DRAWING VIEWS

In the figures.

DETAILED DESCRIPTION OF THE INVENTION

Figure 1:
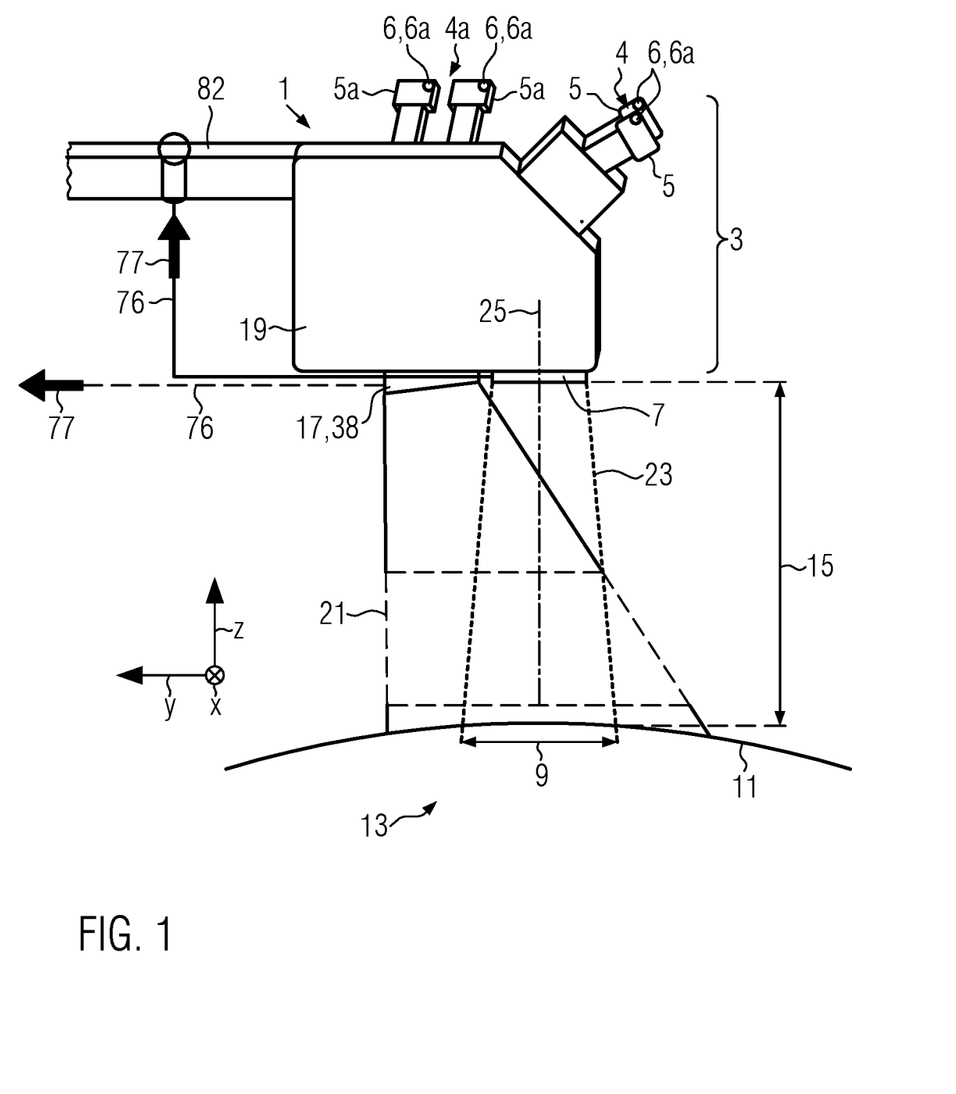
FIG. 1 shows a schematic side view of a first embodiment of the inventive surgical microscope.

FIG. 1 shows a schematic side view of a first embodiment of an inventive surgical microscope 1, which surgical microscope 1 comprises an optical imaging system 3, which optical imaging system 3 comprises, for instance, a stereoscopic eyepiece 4 comprising eyepieces 5, a stereoscopic assistant's eyepiece 4a comprising assistant's eyepieces 5a located at the side of the surgical microscope 1 and an objective 7. The optical imaging system 3 determines a field of view 9 which is a portion of the inspection area 11 which may be a patient 13.

The field of view 9 is determined by the numerical aperture of the optical imaging system 3 and a working distance 15, which working distance 15 is measured along a z-axis. The field of view 9 extends along the x-axis and y-axis.

The surgical microscope 1 further comprises a gesture detection unit 17 which is attached to the housing 19 of the surgical microscope 1. The gesture detection unit 17 acts as a reference point 38 in the embodiments shown in FIG. 1. In other embodiments the reference point 38 may for instance be located in the inspection area 11.

The eyepieces 5 and the assistant's eyepieces 5a comprise sensors 6 which detect whether one of the eyepieces 5, 5a is used for viewing the imaged field of view 9. The sensors 6 are proximity sensors 6a in the embodiment shown.

The gesture detection unit 17 comprises two signal lines 76, wherein one signal line 76 is an electrical line (solid) and a second signal line 76 is a wireless connection (dashed). Via those two signal lines 76, a control signal 77, illustrated by an arrow, is transmitted.

The signal line 76 indicated by the solid line is connected to a moveable mechanical component which is a joint 82a of a holding arm 82b which holds the surgical microscope 1.

The gesture detection unit 17 is tilted around the x-axis and faces towards the field of view 9, such that a gesture detection zone 21 at least partially overlaps with the viewing section 23 of the optical imaging system 3. The viewing section 23 is indicated by a dashed surrounding line.

The objective 7 defines an optical axis 25 which is oriented parallel to the z-axis. It is noted that the optical axis 25 is oriented according to the objective 7 and not necessarily to further components (e.g. the eyepiece 5) of the optical imaging system 3.

In FIG. 1, it is shown that the detection zone 21, which is a 3D-volume, is located at a distance to the field of view 9 of the inspection area 11. Only the movement of an object (not shown) within the surrounded volume inside the dashed line is detected, i.e. movements of an object above (with reference to the z-axis) or below the detection zone 21 will be ignored and will not generate a control signal.

Figure 2:
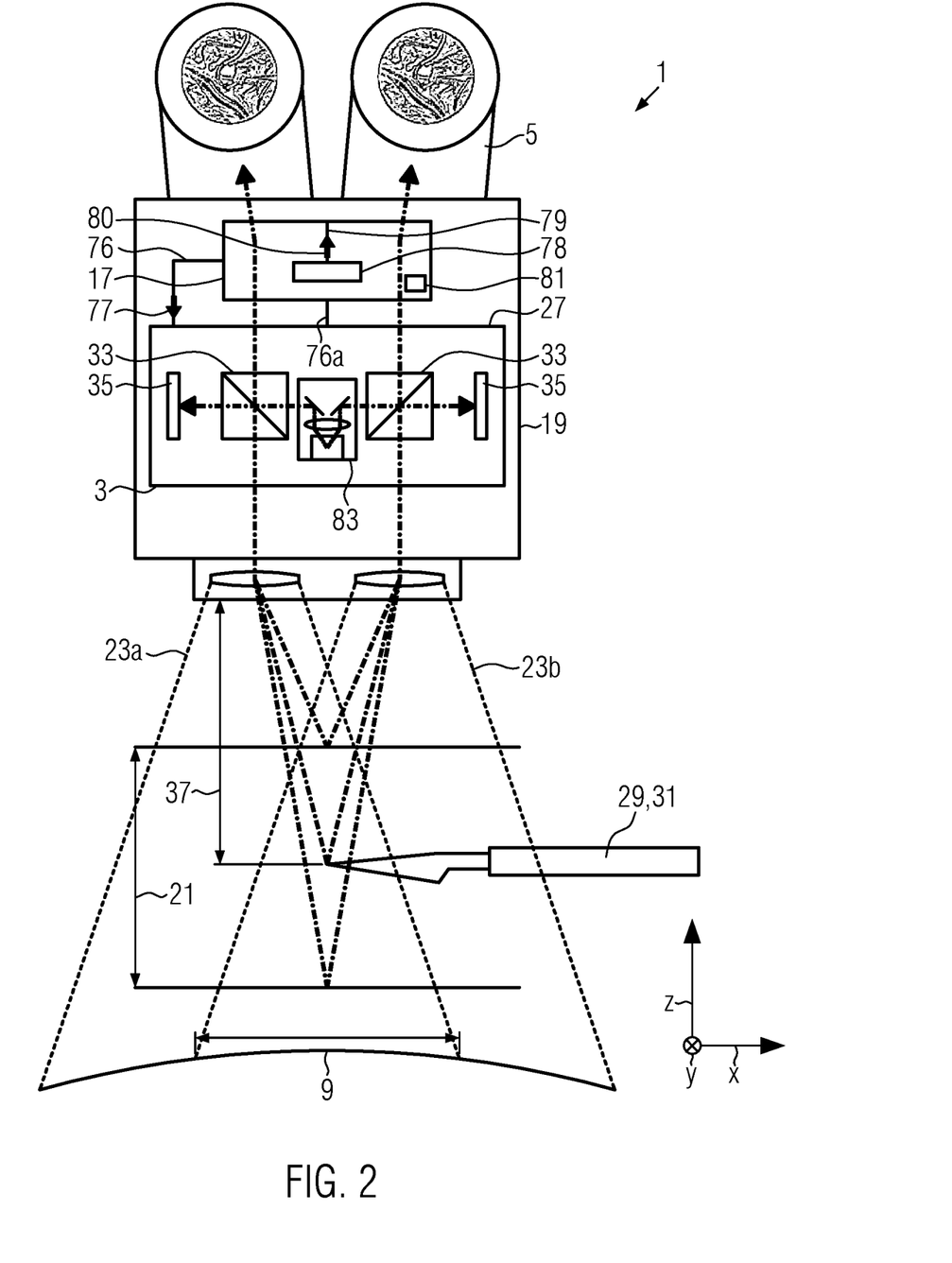
FIG. 2 shows a schematic front view of a second embodiment of the inventive surgical microscope.

FIG. 2 shows a schematic front view of a second embodiment of the inventive surgical microscope 1 in which the gesture detection unit 17 is embodied integrally in the housing 19 of the surgical microscope 1. This embodiment does not comprise the stereoscopic assistant's eyepiece 4a.

In the embodiment shown in FIG. 2, the 3D-camera 27 of the surgical microscope 1 provides the distance information of objects 29 via a signal line 76.

The gesture detection unit 17 further comprises a movement detection module 78, which is provided by the signal line 76a with data from the 3D-camera 27.

The movement detection unit 78 provides a movement-data signal 80 via a movement-data line 79 to the gesture detection unit 17.

Via the signal line 76, the gesture detection unit 17 outputs a control signal 77 to the optical imaging system 3. The control signal 77 and the movement-data signal 80 are indicated by arrows.

The gesture detection unit 17 further comprises a relationship mapping unit 81, which maps a detected movement 65 with an operation to be performed by the optical imaging system 3 or the moveable mechanical component 82.

The surgical microscope 1 further comprises a projection unit 83, which is adapted to project additional and/or interactive images 71 (not shown) onto the imaged inspection area. In the embodiment shown, the projection unit 83 utilizes the beam splitters 33 for being optically coupled to the optical imaging system 3.

In FIG. 2, the object 29 is a scalpel 31, which is located inside the detection zone 21 and whose movements are detected by the gesture detection unit 17.

The 3D-camera 27 is only schematically shown, whereas only the beam splitters 33 and the 2D-sensors 35 are indicated. The 2D-sensors may be CCD cameras. Due to the different viewing sections 23a and 23b of the two channels, a three-dimensional image of the field of view 9 may be generated, imaged and viewed via the eyepiece 5.

In the embodiment of the surgical microscope 1 shown in FIG. 2, the gesture detection unit 17 receives data from the 3D-camera 27, in particular from the 2D-sensors 35 and assesses the distance data of the scalpel 31, whereas the distance data corresponds to the distance 37 of the tip of the scalpel 31.

The surgical microscope 1 of FIG. 2 does not comprise a stereoscopic assistant's eyepiece 4a.

Figure 3:
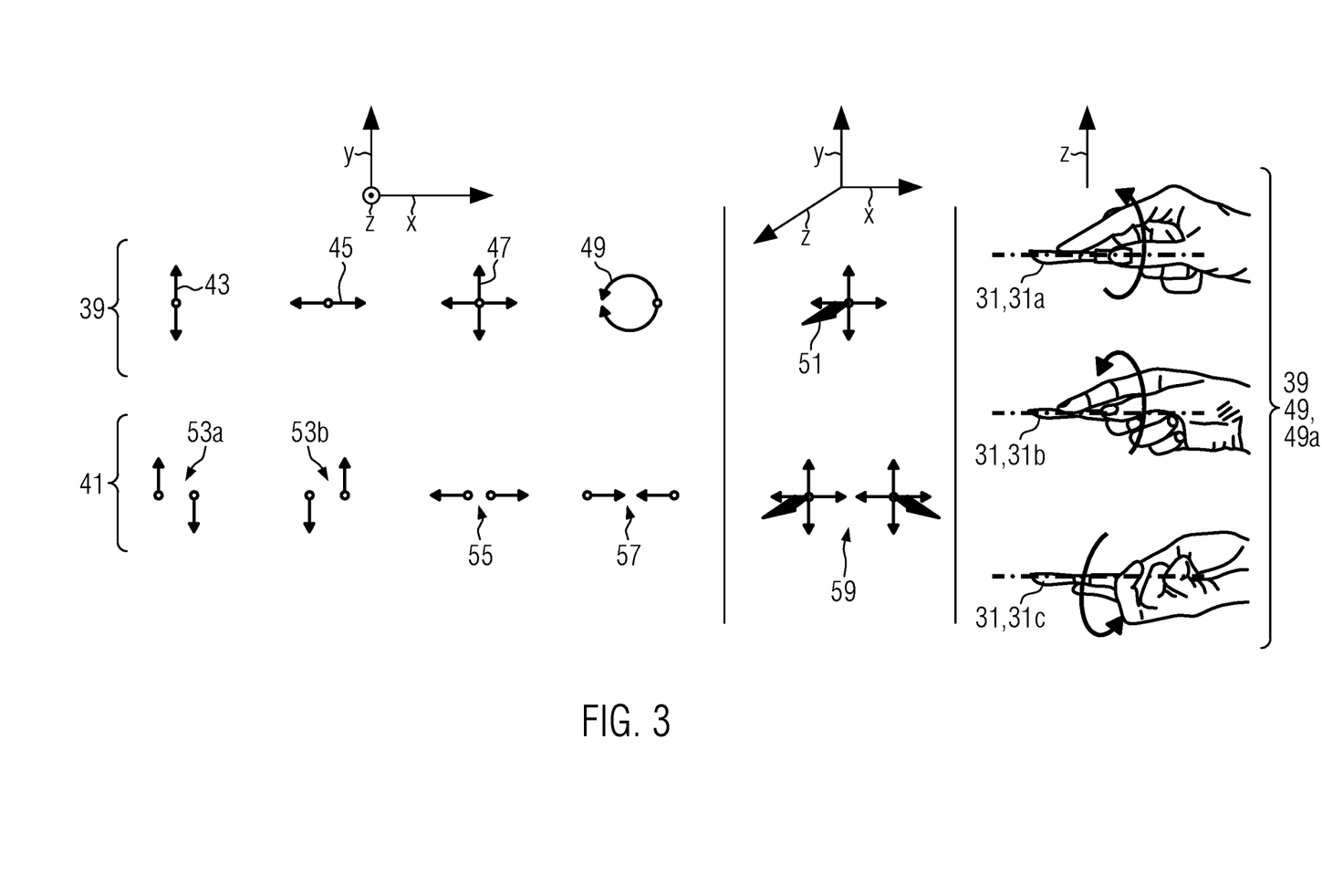
FIG. 3 shows different possible movement patterns of the object.

FIG. 3 shows a schematic drawing illustrating different movement patterns of the object (not shown) whereas one may distinguish one hand-gestures 39 and two-hand gestures 41.

Possible one-hand gestures 39 are movements of the objects along the y-axis, for instance a vertical gesture 43, a horizontal gesture 45, a combined 2D-gesture 47, a circular gesture 49 and an upward gesture 51 during which the object is moved along the z-direction in a positive sense of the z-axis.

Possible two-hand gestures 41 are displacement gestures 53a and 53b, a zoom-in gesture 55 and a zoom-out gesture 57.

A possible two-hand gesture 41 along the z-axis is shown in case of the second upward gesture 59, in which both objects (not shown) are moved along the z-direction, whereas the drawn arrows are pointing in different directions due to the perspective chosen for the figure.

FIG. 3 furthermore shows a rotational gesture 49a, which is one possible one-hand gesture 39 and a circular gesture 49 as well. The rotational gesture 49a is performed in the x-y plane by rotating the scalpel 31 from a first rotational position 31a to a second rotational position 31b and into a third rotational position 31c.

Figure 4:
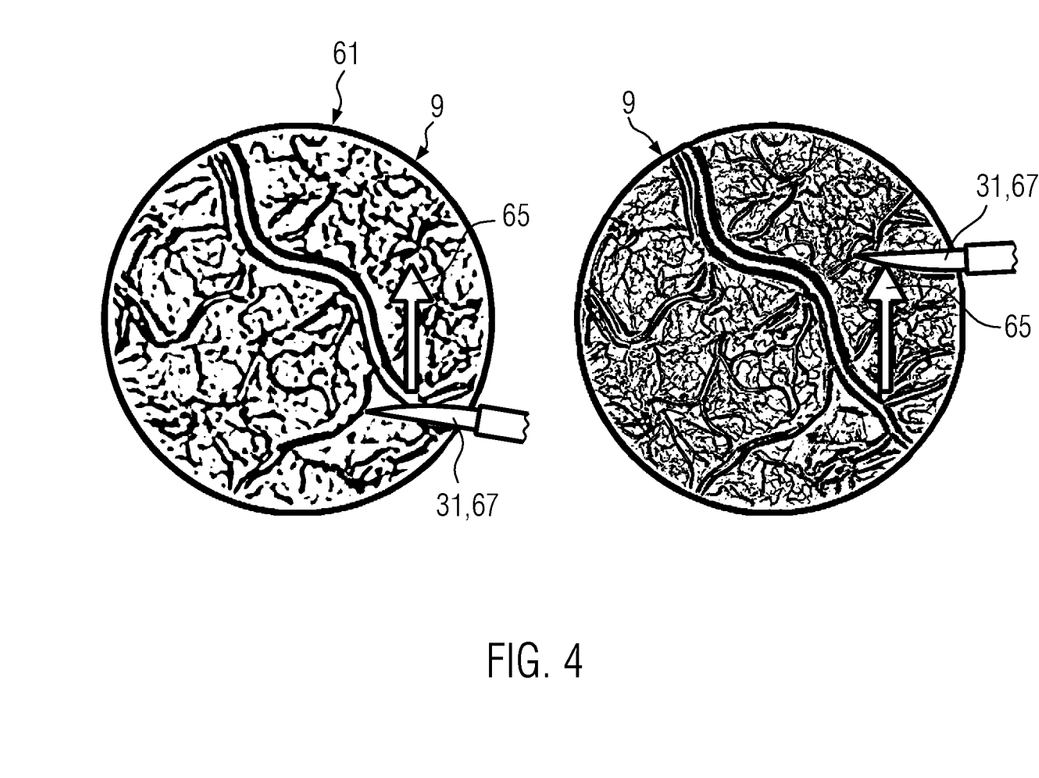
FIG. 4 shows an exemplary adjustment of the working distance of the inventive surgical microscope.

FIG. 4 shows an exemplary operation which is performed by the optical imaging system depending on the movement of a scalpel 31.

FIG. 4 shows the image of the field of view 9 in two states of the optical imaging system 3. In the unfocused state 61 the image is blurred due to an incorrect working distance and consequently misaligned focus of the surgical microscope 1.

In the unfocused state 61, the scalpel 31 is located in the detection zone 21, which is, however not visible in FIG. 4 (see for instance FIG. 2), i.e. movements of the scalpel 31 are detected by the gesture detection unit 17 (not shown), which in turn generates a control signal for altering the state of the optical imaging system 3.

The scalpel 31 performs a movement 65 which is indicated by an arrow, which movement 65 starts at a start position 67 and ends at an end position 69 of the scalpel 31.

The detected movement generates a control signal which controls the working distance of the optical imaging system 3 and which control signal initiates change of the working distance 15 of the optical imaging system 3, which in turn adjusts the focus of the surgical microscope 1.

If the scalpel 31 is moved from the start position 67 to the end position 69, the movement 65 of the scalpel 31 is detected as an online gesture, i.e. the surgeon directly sees the change of the state of the surgical microscope 1 during the movement 65.

Upon arriving at a focused state 63 of the field of view 9 imaged by the optical imaging system 3, the surgeon stops the movement of the scalpel, which stopped position corresponds to the end position 69.

Figure 5:
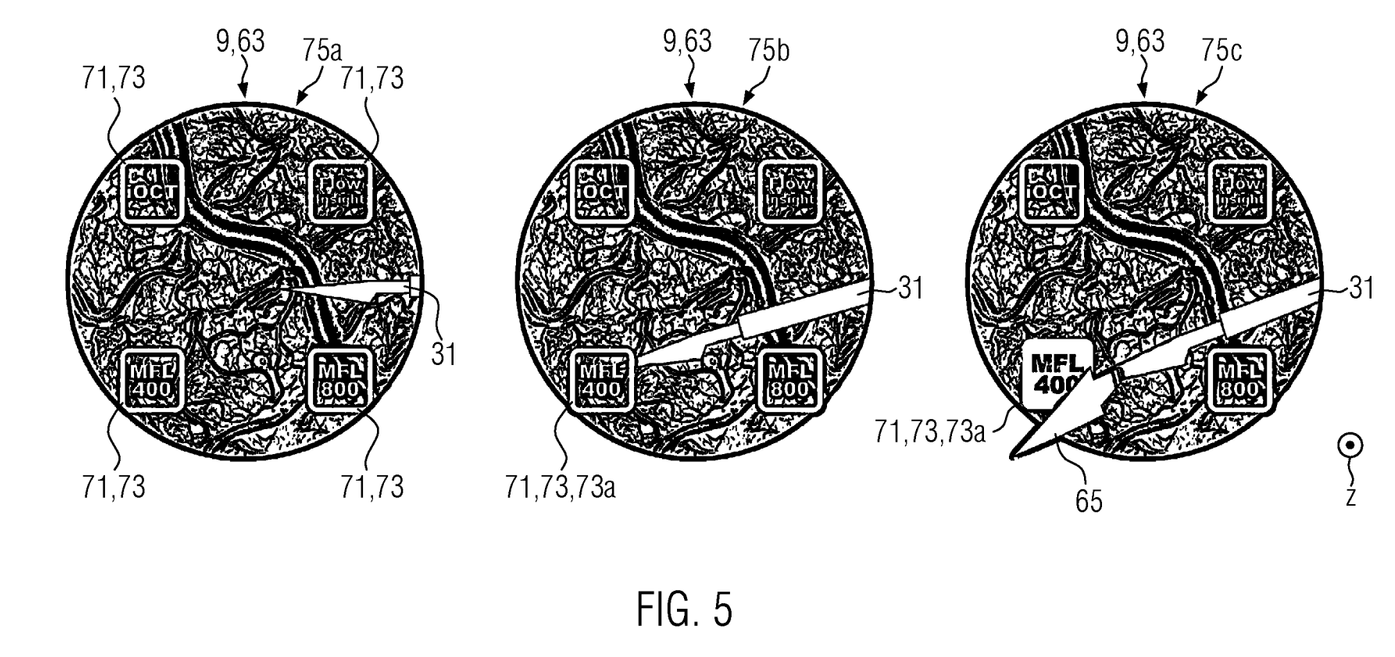
FIG. 5 shows an exemplary application of one of four interaction portions for selection of an imaging note.

FIG. 5 shows an exemplary application of interaction portions for selecting one out of several imaging modes.

In FIG. 5, the same field of view 9 of a focused state 63 is shown, where a projection unit (not shown) projects four opaque images 71 in an overlaying manner on the imaged inspection area, which images 71 define interaction portions 73 of the field of view 9. The images 71 and interaction portions 73 are solely labeled in the first view 75a shown in FIG. 5.

The images 71 contain a visual feedback of the operation of the optical imaging system 3 which can be activated by the corresponding interaction portion 73.

In FIG. 5, the shown interaction portions 73 correspond to different imaging modes, wherein in the first view 75a, the scalpel 31 is positioned outside the interaction portions 73 and subsequently moved into the left lower interaction portion 73a, which is shown in the second view 75b.

In the third view 75c, a movement 65 of the scalpel 31 out of the drawing plane, i.e. along the z-axis is indicated by an arrow. This gesture is detected by the gesture detection unit 17 (not shown), which gesture detection unit 17 generates a control signal processed by a computing unit (not shown), which subsequently initiates change of the imaging mode to the one corresponding to the according left lower interaction portion 73a.

The imaging mode selected in FIG. 5 in the third view 75c is the mode 'MFL 400' and after recognition of the movement 65 of the scalpel 31, the detection of the movement 65 for activating the function corresponding to the left lower interaction portion 73a is indicated by projecting an alternate, i.e. modified, image 71 in the left lower interaction portion 73a.

The movement 65 shown in the third view 75c is an offline movement, i.e. the operation corresponding to the activation of the according interaction portion 73 is only performed after completion of the movement 65.

As already mentioned in the beginning of the explanation of the figures, the embodiment shown in FIGS. 1-5 are to be understood as exemplary and do not limit the scope of protection of the present disclosure. Therefore, any number of interaction portions 73, one-hand gestures 39, two-hand gestures 41 and functional sections of the field of view 9 are conceivable.

REFERENCE NUMERALS 1 surgical microscope
3 optical imaging system
4 stereoscopic eyepiece
4a stereoscopic assistant's eyepiece
5 eyepiece
5a assistant's eyepiece
6 sensor
6a proximity sensor
7 objective
9 field of view 11 inspection area
13 patient
15 working distance
17 gesture detection unit
19 housing
21 detection zone
23, 23a, 23b viewing section
25 optical axis
27 3D-camera
29 object
31 scalpel
31a first rotational position
31b second rotational position
31c third rotational position
33 beam splitter
35 2D-sensor
37 distance
38 reference point
39 one-hand gestures
41 two-hand gestures
43 vertical gesture
45 horizontal gesture
47 combined 2D-gesture
49 circular gesture
49a rotational gesture
51 upward gesture
53a, 53b displacement gestures
55 zoom-in gesture
57 zoom-out gesture
59 second upward gesture
61 unfocused state
63 focused state
65 movement
67 start position
69 end position
71 image
73 interaction portion
73a left lower interaction portion
75a first view
75b second view
75c third view
76, 76a signal line
77 control signal
78 movement detection module
79 movement-data line
80 movement-data signal
81 relationship mapping unit
82 moveable mechanical components
82a joint
82b holding arm
83 projection unit
x x-axis
y y-axis
z z-axis

What is claimed is:

1. A surgical microscope having a field of view and comprising an optical imaging system which is configured to image an inspection area which is at least partially located in the field of view,
wherein the surgical microscope further comprises a gesture detection unit configured to detect a movement of an object by optical detection between the optical imaging system and the inspection area, the gesture detection unit is connected to the optical imaging system via a signal line,
wherein the gesture detection unit is configured to output a control signal via the signal line to the optical imaging system depending on the movement of the object, the optical imaging system being configured to alter its state depending on the control signal, wherein the gesture detection unit defines a detection zone which is located between the inspection area and the optical imaging system and which detection zone is spaced apart from the inspection area, wherein gesture detection of the gesture detection unit is limited to movements of the object in the detection zone,
wherein the optical imaging system comprises a projection unit, which projection unit is optically connected to the optical imaging system and which projection unit is adapted to project interactive images on at least one interaction portion, wherein the at least one interaction portion at least partially overlaps with the imaged inspection area, and
wherein the surgical microscope is configured to compare the position of the object with the position of the at least one interaction portion of the imaged inspection area and load a first relationship map for access by the gesture detection unit if the object is detected in a detection zone outside the interaction portion and load a second relationship map for access by the gesture detection unit if the object is detected to be located within the interaction portion, the first relationship map and the second relationship map each comprising a corresponding set of predetermined movement patterns respectively associated with a corresponding set of control signals outputted in response to the predetermined movement patterns, the second relationship map comprising a different set of predetermined movement patterns as compared to the first relationship map.

2. The surgical microscope according to claim 1, wherein the detection zone overlaps the inspection area at least in sections.

3. The surgical microscope according to claim 1, wherein the gesture detection unit further comprises a movement detection module for differentiating three-dimensional movements of the object in the detection zone, which movement detection module is connected to the gesture detection unit via a movement-data line and which movement detection module is adapted to output a movement-data signal via the movement-data line to the gesture detection unit depending on the movement of the object.

4. The surgical microscope according to claim 3, wherein the gesture detection unit further comprises a relationship mapping unit which is connected to the movement detection module via the movement-data line and which relationship mapping unit is adapted to map relationships between the movement of the object and the control signal, which control signal is provided via the signal line to the optical imaging system.

5. The surgical microscope according to claim 1, wherein the optical imaging system comprises moveable mechanical components, wherein the optical system is configured to alter its state depending on the control signal by moving one or more of the moveable mechanical components.

6. The surgical microscope according to claim 1, wherein the object is one of a finger and a tool.

7. A method for a gesture control of a surgical microscope having a field of view and an optical imaging system, wherein the optical imaging system images an inspection area which is at least partially located in the field of view, wherein the method comprises the steps of
contactlessly and optically detecting by a gesture detection unit a movement of an object with respect to a reference point, wherein the movement of the object is detected between the optical imaging system and the inspection area;

controlling the optical imaging system depending on the movement of the object by outputting a control signal from the gesture detection unit to the optical imaging system;

and wherein the method further comprises the steps of
projecting at least one interactive image onto at least one interaction portion of an imaged inspection area;
comparing the movement of the object with predetermined interaction movement patterns; and
controlling the optical imaging system and/or the surgical microscope depending on the movement of the object within the at least one interaction portion,
wherein the method is adapted to compare the position of the object with the position of the at least one interaction portion of the imaged inspection area and load a first relationship map for access by the gesture detection unit if the object is detected in a detection zone outside the interaction portion and load a second relationship map for access by the gesture detection unit if the object is detected to be located within the interaction portion, the first relationship map and the second relationship map each comprising a corresponding set of predetermined movement patterns respectively associated with a corresponding set of control signals outputted in response to the predetermined movement patterns, the second relationship map comprising a different set of predetermined movement patterns as compared to the first relationship map, and
wherein the detection zone is located between the inspection area and the optical imaging system and which detection zone is spaced apart from the inspection area, wherein gesture detection of the gesture detection unit is limited to movements of the object in the detection zone.

8. The method according to claim 7, wherein the method further comprises the step of providing distance and/or movement data of the object to a computing unit.

9. The method according to claim 7, wherein the method further comprises the step of differentiating the detected movement of the object.

10. The method according to claim 7, wherein the method further comprises the step of comparing the movement of the object with predetermined movement patterns.

11. The method according to claim 7, wherein the method further comprises the step of controlling moveable mechanical components of the surgical microscope depending on the movement of the object.

12. The method according to claim 7, wherein the method further comprises the steps of
optically detecting the object;
comparing the detected object with predetermined object patterns for determination of the type of the object; and
selecting one of at least two relationship maps according to the type of the object.

13. The method according to claim 7, wherein the object is one of a finger and a tool.

14. The method according to claim 7, wherein the reference point is on the gesture detection unit.

15. The method according to claim 7, wherein the step of contactlessly and optically detecting the movement of the object with respect to the reference point includes contactlessly detecting a distance of the object from the reference point.

16. A non-transitory computer-readable storage media storing a computer program comprising instructions which, when the instructions are executed by a processor, cause the processor to perform the method of claim 7.

* * * * *